United States Patent
Bauer et al.

(10) Patent No.: US 6,320,641 B1
(45) Date of Patent: Nov. 20, 2001

(54) HIGH-PRECISION-RESOLUTION IMAGE ACQUISITION APPARATUS AND METHOD

(75) Inventors: Heino G. Bauer, Auenwald (DE); Robert B. Schoenberger, Alexandria, VA (US); David J. Siviter, Arnold, MD (US)

(73) Assignee: Agris-Schoen Vision Systems, Inc., Alexandria, VA (US)

( * ) Notice: Subject to any disclaimer, the term of this patent is extended or adjusted under 35 U.S.C. 154(b) by 0 days.

(21) Appl. No.: 09/402,245

(22) PCT Filed: Apr. 1, 1998

(86) PCT No.: PCT/US98/06500

§ 371 Date: Oct. 1, 1999

§ 102(e) Date: Oct. 1, 1999

(87) PCT Pub. No.: WO98/44718

PCT Pub. Date: Oct. 8, 1998

Related U.S. Application Data

(60) Provisional application No. 60/042,525, filed on Apr. 1, 1997.

(51) Int. Cl.[7] .............................. G03B 27/00; G03B 27/52
(52) U.S. Cl. ................................. 355/18; 355/55
(58) Field of Search .................. 355/18, 53, 55, 355/56; 396/428; 348/87, 94, 95; 356/375, 399–400

(56) References Cited

U.S. PATENT DOCUMENTS

| | | |
|---|---|---|
| 1,349,336 | 8/1920 | Haddock . |
| 2,312,261 | 2/1943 | Mills . |
| 2,316,751 | 4/1943 | Adler, Jr. . |
| 2,337,463 | 12/1943 | Hall . |
| 2,376,082 | 5/1945 | Pullen . |
| 2,379,698 | 7/1945 | Fischer . |
| 2,388,714 | 11/1945 | Schwartz et al. . |
| 2,397,160 | 3/1946 | Schwartz et al. . |
| 2,403,308 | 7/1946 | Schwartz et al. . |
| 2,677,998 | 5/1954 | Schwartz et al. . |
| 3,010,019 | 11/1961 | Sohst . |
| 3,117,480 | 1/1964 | Peddinghaus . |
| 3,418,908 | 12/1968 | Land . |
| 3,610,128 | 10/1971 | Bellows . |
| 3,836,919 | 9/1974 | Matsumoto et al. ................. 95/44 C |
| 4,435,055 | * 3/1984 | Berdat et al. ............................ 354/4 |
| 4,836,671 | 6/1989 | Bautista . |
| 4,856,894 | 8/1989 | Anderson . |
| 5,289,220 | 2/1994 | Fidler et al. ......................... 354/165 |
| 5,379,106 | * 1/1995 | Baldur ................................. 356/375 |
| 5,539,514 | * 7/1996 | Shishido et al. ..................... 356/237 |
| 5,550,364 | 8/1996 | Rudeen ................................ 235/462 |
| 5,574,577 | * 11/1996 | Wally et al. ......................... 358/487 |
| 5,598,007 | 1/1997 | Bunce et al. ......................... 250/566 |
| 5,619,031 | * 4/1997 | Choate ............................. 250/201.2 |
| 5,627,630 | 5/1997 | Rudeen ................................ 235/462 |
| 5,734,153 | 3/1998 | Swartz et al. ........................ 235/472 |

OTHER PUBLICATIONS

Taku, "Close–up Photography Camera", Document Bibliography and Abstract, JP8082738, Mar. 26, 1996.
"Edmonds Scientific Catalogue", Video/Imaging Testing Targets, p. 225.
"Lightning Powder Company, Inc.", Apr. 1, 1999, Sections 6, pp. 1–22, Section 7, pp. 1–8.

\* cited by examiner

*Primary Examiner*—Russell Adams
*Assistant Examiner*—Henry Hung Nguyen
(74) *Attorney, Agent, or Firm*—Pillsbury Winthrop LLP

(57) ABSTRACT

A method and apparatus for setting and repeatably and reliably maintaining a desired image resolution. The invention features an optical, image acquiring device and a pair of light sources, the beams from which are caused to converge at a distance from the optical device which provides the desired resolution. Subsequently, positioning the optical device with the point of convergence of the beams on the surface of an object being imaged ensures the desired resolution. In preferred embodiments, the plane yielding the desired resolution is caused to be coincident with the plane of optimal focus.

32 Claims, 8 Drawing Sheets

Top of Block

Bottom of Block

HIGH-PRECISION-RESOLUTION IMAGE ACQUISITION APPARATUS AND METHOD

This application claims benefit of Provisional application Ser. No. 60/042,525 filed Apr. 1, 1997.

FIELD OF THE INVENTION

The invention relates in general to image acquisition using a camera and, in particular, to an apparatus and method used to set and maintain the resolution of an image with a high degree of precision.

BACKGROUND OF THE INVENTION

In certain situations, it is necessary or desirable to know and to be able to reproduce repeatedly and reliably the resolution of an image captured on a medium. In the context of an image captured on film, i.e., as a conventional photograph, the term "resolution" is analogous to the scale of the photograph and indicates how a distance or dimension measured "off of" the photograph corresponds to the distance or dimension in the scene or object that has been photographed. In the context of digital image acquisition using, e.g., a digital "photographic" or "still" camera or a digital video camera, the term "resolution" refers to the number of pixels in the image corresponding to a distance or dimension in the scene or oject being "photographed" or monitored, typically referred to as image pixels per object inch or, more conveniently, dots per inch ("dpi").

One such application where it is necessary to know the resolution of an image (object inch per photograph inch in a film-based photograph or dots per object inch (dpi) in a digital image) relates to photographing fingerprints, e.g., for purposes of crime investigation. When fingerprints are photographed using a conventional, film-based camera, the person taking the picture typically puts an object of known size ("reference object"), e.g., a ruler or a coin, in the field of view with the fingerprint target. Dimensions within the fingerprint, e.g., from one fingerprint landmark to another, are then calculated by measuring the distance as shown in the photograph and scaling that distance (as shown in the photograph) either up or down, the scale factor being equal to the known, actual size of the reference object divided by the size of the reference object as shown in the photograph. Similarly, if a digital camera is used (either still ("photographic") or video), the relevant distance is determined by measuring it in the image in terms of pixels, and then multiplying the number of pixels by an appropriate scale factor expressed in terms of length per pixels, the scale factor being equal to a known dimension of the reference object divided by the number of pixels in the image corresponding to that known dimension.

Calibrating the resolution of the image in this manner can be time-consuming, difficult, and therefore inaccurate. Accordingly, there is a need for an apparatus and method to facilitate recording an image with a known resolution, and doing so repeatedly and reliably.

SUMMARY OF THE INVENTION

The present invention fulfills this need. In general, the invention provides an apparatus and method by which a camera—preferably a digital video camera—can be positioned with respect to an object being imaged, with the resolution consistently and easily being maintained at a desired value. Furthermore, in preferred embodiments of the invention, the camera can be positioned such that the plane of optimal focus, typically at the center of the depth of field, is coincident with the plane of view having the required resolution.

In general, this is achieved with an apparatus in which the distance from the camera to a target object can be adjusted and then held fixed. The apparatus uses two or more light sources, e.g., lasers, collimated lights, spotbeams, slit lamps, etc., whose light axes can be pivoted such that their beams of light intersect at the surface of the target object. The light sources, which are held at fixed distances from the camera, can be locked into the particular angular orientation with respect to the camera. With this apparatus, once the resolution is set, that resolution can be regained for any subsequent object placed in front of the camera, regardless of its dimension or size, simply by moving the camera with respect to the new object until the light beams once again intersect at the surface of the new object. Alternatively, a single light source can be used and the camera is moved with respect to the new object until the point at which the light beam strikes the new object is at the same location within the field of view of the camera.

The apparatus includes a support surface which supports an object that is to be imaged, and the camera is supported at an optical distance from the support surface (i.e., from the object). The optical distance from the object to the camera is adjustable such that the resolution of an image of the object can be adjusted. The apparatus further includes a light source which projects a beam of light onto the object. The light source is configured such that the location where the beam of light strikes the object varies as the optical distance is varied.

Preferred embodiments of the invention may include one or more of the following features. Preferably, the apparatus is configured such that the beam of light is angled relative to the optical path (axis) along which the image of the object being observed is acquired. Preferably, the apparatus includes two light sources, both of which may be angled relative to the optical path such that the beams of light projected thereby can be rotated so as to intersect at the surface of the object being imaged.

Preferably, the light source or sources is or are lasers, and where two lasers are used, it is preferable for one of them to be a line laser with the other being a more conventional laser which projects a dot or spot of light. This permits the two beams to be distinguished more easily, thereby facilitating adjustment of the optical distance based on the relative positions of where the beams strike the surface of the object.

Preferably, the apparatus includes computer hardware and software for analyzing a signal generated and output by the camera. The signal can be analyzed to determine the resolution of the image acquired by the camera, which resolution may be expressed in terms of pixels per unit of length of the object being imaged (dpi).

In further contemplated embodiments, the apparatus includes a motor which adjusts the optical distance between the camera and the support surface and/or motors which adjust the angle of the light source or sources relative to the optical path. With such motors, the image can be analyzed by computer and the motors can be controlled by the computer to adjust a) the optical distance (whether to achieve a desired resolution during calibration or to return to that desired resolution subsequently); and/or b) the angle of the light beam or beams relative to the optical path such that a single beam strikes the surface of an object being imaged at a desired location (e.g., in the center of the field of view) or such that two beams converge at the surface of the object being imaged.

In still further contemplated embodiments, the apparatus may include and x-y-θ support platform to facilitate precise positioning of the object being imaged. Furthermore, the light sources preferably are interlocked with the camera such that they are turned off when the image of an object is actually being acquired.

In another aspect, the invention features a method for acquiring the image of an object with a repeatable resolution. The method includes the steps of providing a camera at an optical distance from an object, the object being positioned within the field of view of the camera. First and second light sources are provided and project beams of light on the surface of the object. One or both of the light sources are adjusted such that the beams of light converge on the surface of the object. The object is then removed from the field of view and a second object is positioned within the field of view of the camera. The optical distance from the camera to the second object is adjusted, as necessary, such that the first and second beams of light converge at the surface of the second object. This guarantees the same resolution of an image of the second object as the resolution of an image of the first object would have been. An image of the second object is then acquired.

In yet another aspect, the invention features a method of acquiring the image of an object with a repeatable resolution. In this aspect, the positioning of the camera (and hence the resolution of the image) is adjusted based on where in the field of view of the camera the point where a beam of light strikes the object lies. This may be done using a single light source and adjusting the optical distance such that the beam of light projected by the single light source strikes the surface of an object being imaged precisely in the center of the field of view of the camera, or using two light sources and adjusting the optical distance such that the two light sources converge at the surface of the object being imaged, the location of the point of convergence lying at the same position within the field of view.

BRIEF DESCRIPTION OF THE DRAWINGS

Preferred embodiments of the invention will now be described in connection with the following drawings, in which.

DETAILED DESCRIPTION OF THE INVENTION

Figure 1:
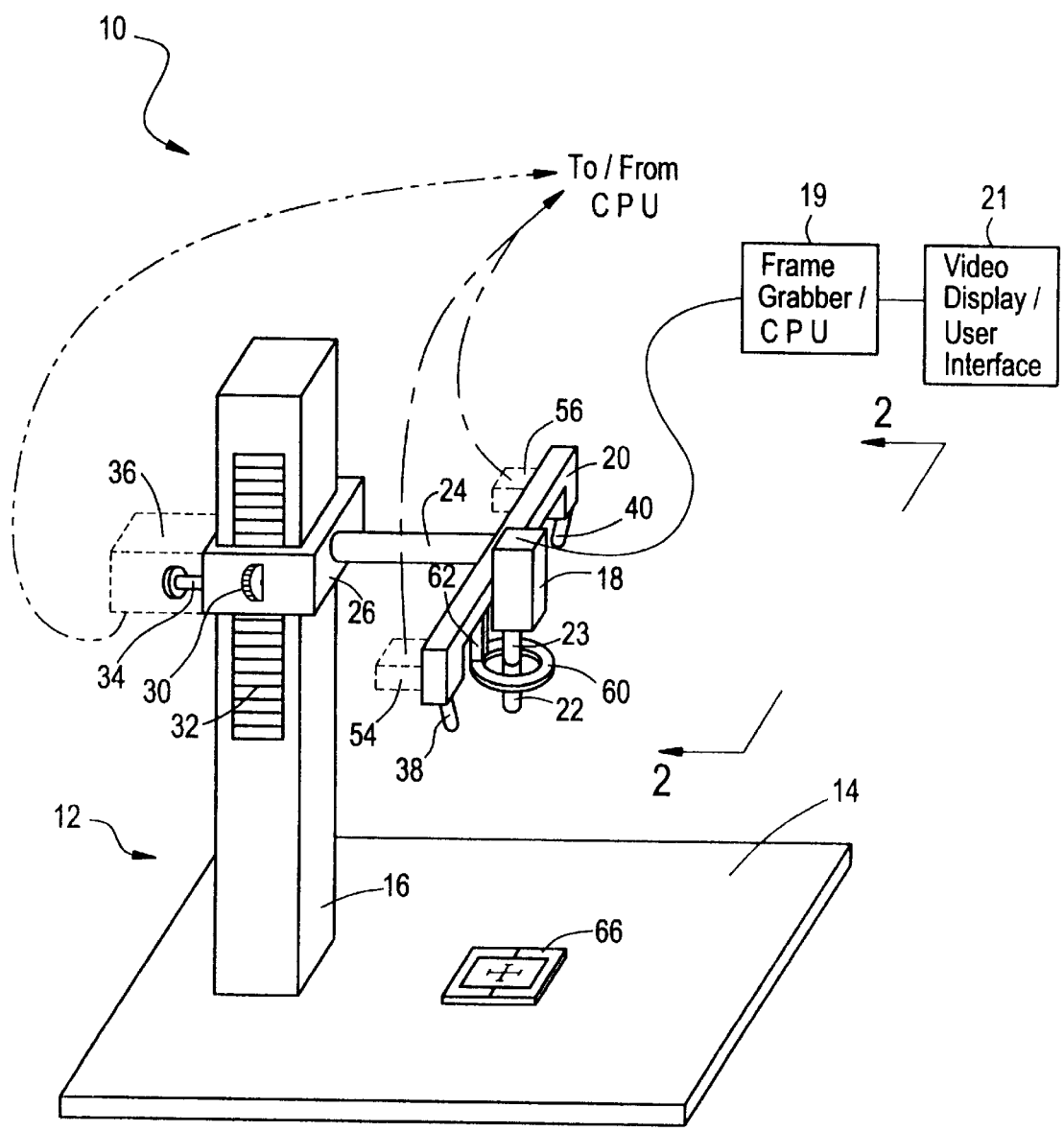
FIG. 1 is a schematic, perspective view showing a high-precision-resolution image acquisition apparatus according to the invention.

An image acquisition apparatus 10 according to the invention is shown in FIG. 1. The apparatus includes a support stand 12, which consists of a flat platform 14 and a camera support post 16. Camera 18 is securely attached to laser mounting bracket 20 via a separate camera "standoff" or support bracket (not visible), with camera lens 22 aimed downward toward the platform 14. In a preferred embodiment, the camera 18 is a Kodak® MASD MEGA-PLUS™ 1.4 i model digital video camera, available from the Motion Analysis Systems Division of the Eastman Kodak Company, and lens 22 is a Componon-S 50 millimeter/F2.8 lens, available from Schneider Optics, Inc. in Hauppauge, N.Y., preferably used with an extension tube 23. The camera outputs an image signal that is sent to frame grabber/central processing unit 19, as described in greater detail below, and video display/user interface 21 displays an image of the object being viewed and allows a user to use the system. The laser mounting bracket 20, along with camera 18, is supported away from the support post 16 by support arm 24. Support arm 24 is securely connected to (or may be formed integrally with) and extends from collar 26. Collar 26 fits over support post 16 and moves up and down along it, thereby varying the distance from the camera 18 to the platform 14. Preferably, a locking device (not shown) such as a large set screw (e.g.

A pinion gear 30 extends through the collar 26 to mate with rack gear 32 formed along the side of support post 16. Pinion gear 30 is turned using hand knob 34, thereby raising or lowering the camera assembly. In an alternative embodiment, depending on the materials used to construct the support post 16, rack gear 32 may be eliminated and friction rollers used instead of pinion gear 30.

In another alternative embodiment, an appropriate drive motor 36, indicated schematically in phantom, may be provided such that raising and lowering of the camera assembly is motorized. In such embodiment, position encoders (not shown) can also be provided. The encoders would provide information to the central processing unit (CPU) or to some other controller, and the CPU or controller would control the vertical positioning of the camera, particularly by monitoring the position and movement of the laser beams (described below) in the image, which is digitized and passed to the CPU as described below.

As further shown in FIG. 1, first and second light sources 38, 40 are mounted at the opposite ends of the laser mounting bracket 20. In a preferred embodiment, the light sources 38, 40 are lasers, one of which preferably is a line laser and the other of which is a more conventional laser which projects a dot of laser light on the surface being illuminated. If this is so, it is preferable for the line laser to be mounted such that the line cast by the laser beam extends parallel to two of the edges of the field of view of the camera 18 and perpendicular to the other two edges of the field of view (assuming a square or rectangular field of view), with the line cast by the line laser being oriented perpendicular to the projection onto the base 14 of a line connecting the two laser light sources such that the laser line may be seen to move laterally as the camera assembly is moved up and down. In alternative embodiments, the light sources 38, 40 may be collimated lights, spot beams, slit lamps, etc.

Figure 2:
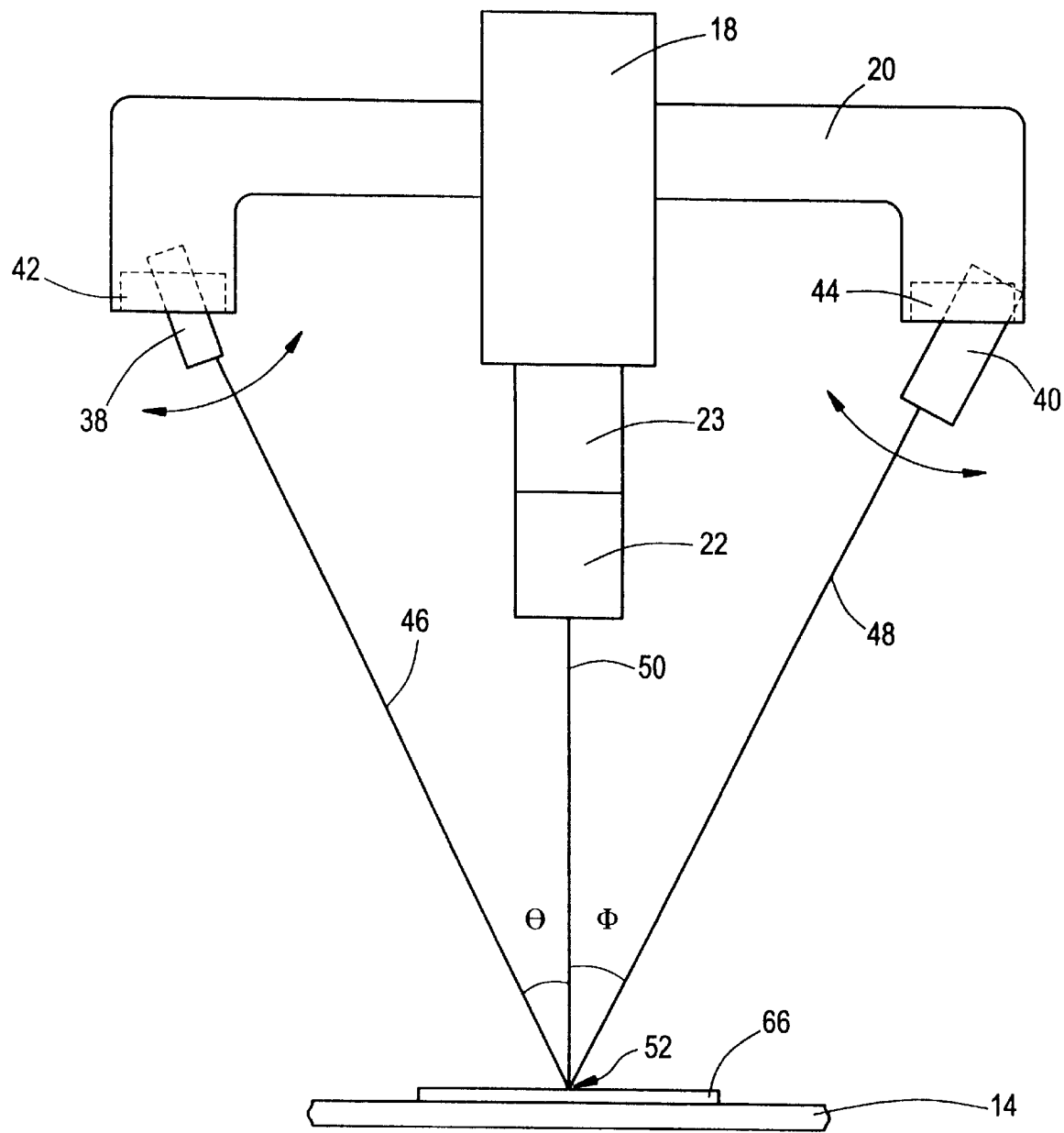
FIG. 2 is a schematic front view, along the lines 2—2 in FIG. 1, of an apparatus according to the invention.

As shown in FIG. 2, light sources 38, 40 are pivotally mounted at the ends of laser mounting bracket 20 on mounting brackets 42, 44, respectively. By pivoting the light sources 38, 40, the angles θ and Φ which laser beams 46, 48 make with respect to the optical axis (path) 50 of the camera are varied, and the location of the point of intersection 52 of the two beams 46, 48 is changed. The lasers should also be pivotable in their respective planes which are oriented perpendicularly to the plane of FIG. 2 and parallel to the optical axis 50. Means (not shown) such as clamps are provided to secure or fix each of the light sources 38, 40 in a given angular position.

In further contemplated embodiments, laser positioning units 54, 56, indicated schematically in phantom (FIG. 1), can be provided to change the angular position of the light sources 38, 40, respectively, by machine as opposed to by hand. Furthermore, angular encoders (not shown) can be provided to measure the angular positions of the light sources 38, 40 and feed that information to the CPU or controller, and that information can be used to control independently the angular position of each of the light sources.

Finally, with respect to the basic structure of the apparatus 10 according to the invention, a light ring 60 preferably is provided. The light ring 60 is supported by arm 62, which is attached to either laser mounting bracket 20 or support arm 24. Light ring 60 is, for example, a fiber optic bundle light ring attached to a halogen light source (not shown) and is used to illuminate the object being imaged, e.g., calibration target 66, the use of which is described below. LED, fluorescent, and high frequency fluorescent lamps are alternatives.

Calibration target 66 is made from a flat piece of metal, such as aluminum, or plastic engraving material (i.e., a thin, flat layer of black plastic that is laminated to a white base layer of plastic) and is cut and marked with precise tolerance, e.a., 0.002 inch (0.05 mm) precision. Alternatively, calibration target 66 can be made by forming the desired calibration pattern on photographic paper, e.g., by exposing and developing a sheet of film, or by forming the pattern from chromium deposited on glass for extremely precise tolerances.

Figure 3:
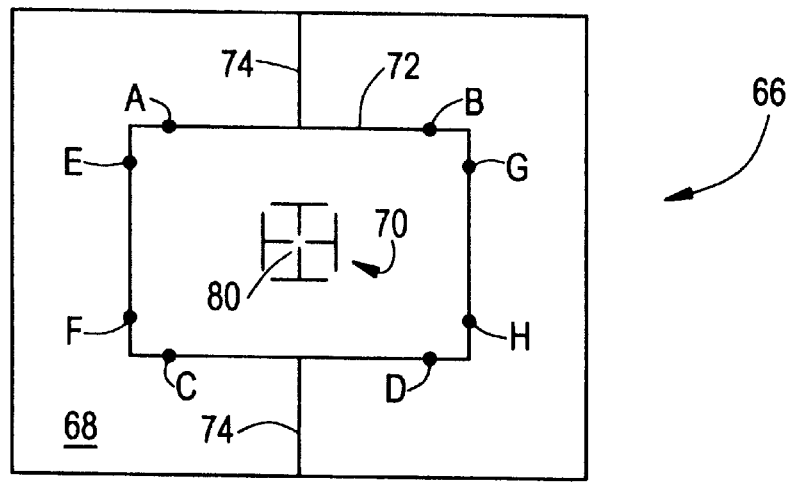
FIG. 3 is a plan view showing the calibration pattern of the calibration target shown in FIG. 1.

A preferred calibration pattern for the calibration target 66 is shown in FIG. 3. Preferably, the surface 68 is primarily black, with the markings being white (ie., the inverse of the pattern as shown in FIG. 3). The markings include cross 70 in the form of a potent cross (see *Miriam Webster's Collegiate Dictionary*, 10th Ed., illustration of "cross"), surrounded by rectangle 72. Preferably, the central intersection portion of the cross 70 is "broken out" to facilitate alignment of the laser beams on the cross, as described below. Alignment hashmarks 74 extend from the rectangle 72 to the edges of the calibration target 66. As noted above, the calibration target is cut and marked with a high degree of precision such that all markings are either perfectly parallel or perfectly perpendicular. Additionally, the dimensions of the markings—particularly the length, width, and marking thickness of the rectangle 72—are precisely known.

The calibration target 66 is used with the apparatus 10 to calibrate the apparatus as follows. Calibration target 66 is placed on support platform 14 beneath the camera 18, and the camera assembly is positioned at a starting height above the target which is, to some extent, arbitrary. The calibration target is generally centered and aligned within the field of view, preferably using a video overlay that is generated and superimposed on the video display/user interface either by the frame grabber or by the video card driving the video display. Preferably, the image acquisition software program indicates the center of the field of view and superimposes this location over the image being shown to the user. The calibration target is then positioned on the platform 14 such that the intersection 80 at the center of the cross 70 lies at the center of the field of view, as can be observed by watching the monitor. The camera is then adjusted to bring the image of the calibration target into focus and the image is acquired.

For certain applications, it may be desirable to use a fixed focus camera—particularly for viewing objects at a specified, standardized resolution. Even for such applications, however, it may still be desirable to use extension tubes (with or without shims) or a back focus mechanism to provide fine tuning of the focus.

In a case where the camera 18 is a film-based photographic (still) camera, a picture of the calibration target is taken and developed. The calibration target markings are then measured as they appear on the photograph and the resolution (scale) of the photographic image is calculated by dividing the dimensions as shown in the photograph by the actual, known dimensions. The camera is then raised or lowered, either manually using knob 34 or, if the apparatus is so equipped, using drive motor 36. This process is repeated until the desired resolution (scale) is obtained.

In the preferred embodiment, however, it is far easier to position the camera such that a desired resolution is obtained. As noted above, the camera 18 in the preferred embodiment is a Kodak® MASD MEGAPLUS™ 1.4 i model digital video camera. With such a camera, an image of the object being monitored, e.g., the calibration target 66, falls on a charge coupled device ("CCD"). The CCD breaks the image down into a matrix (two-dimensional array) of square pixels, each pixel having an associated x- and y-, Cartesian coordinate, and produces a digital signal consisting of light intensity information for each of the pixels. In the preferred embodiment, the picture (image) information from the camera is passed to the CPU through the frame grabber, e.g., a Coreco® Oculus F/64™ model frame grabber available from Coreco Incorporated in St. Laurent, Quebec, Canada, which compiles the digitized, pixilated image information a frame at a time. The digitized image information is then analyzed by an appropriate software package designed to work with the frame grabber information, e.g., (N) AFIS Acquire™, an image acquisition/analysis and "machine vision" software package produced by Agris-Schoen Visions Systems, Inc. in Alexandria, Va.

The (N) AFIS Acquire™ software package is designed to work with the calibration pattern shown in FIG. 3. The program searches the image for the rectangle 72 and, once it locates the rectangle, identifies (but does not necessarily display) points A–H along the rectangle. By way of example, points A and B are each located one eighth of the length of the upper side of the rectangle (as shown in FIG. 3) from the left and right sides of the rectangle, respectively. Similarly, points C and D are each located one eighth of the length of the lower side of the rectangle from the left and right sides of the rectangle, respectively; and points E and G and points F and H are located one eighth of the length of the left and right sides of the triangle from the top and bottom sides of the rectangle, respectively. In general, the important feature is that the points in each pair of points located across the rectangle from each other be the same distance from the respective side or top or bottom edges of the rectangle such that the line segment connecting them is parallel or perpendicular to all four edges of the rectangle.

Once the program locates points A–H, it determines the number of pixels from point A to point C, point B to point D, point E to point G, and point F to point H by calculating the square root of the sum of the squares of the x-coordinate and y-coordinate differences for the two points in each pair, i.e., by the Pythagorean theorem. The program then calculates overall resolution by dividing the number of pixels from point A to point C by the known distance (precisely 1.9 inches (4.826 cm)) from point A to point C; by dividing the number of pixels from point B to point D by the known distance (precisely 1.9 inches (4.826 cm)) from point B to point D; by dividing the number of pixels from point E to point G by the known distance (precisely 2.4 inches (6.096 cm)) from point E to point G; and by dividing the number of pixels from point F to point H by the known distance (precisely 2.4 inches (6.096 cm)) from point F to point H and then averaging these four values.

In further contemplated embodiments, the program would be more flexible and interactive, allowing the user to select (e.g., by pointing and clicking) points from which to calculate resolution. Such points could be offered as possibilities by the program, or they could be selected at the user's discretion, assuming the user provides the program with the known, actual distance between points—for example, if a ruler were being used as the calibration target.

As noted above, the MASD MEGAPLUS™ 1.4 i model digital video camera produces an image with square pixels. If the pixels were rectangular, the program would calculate horizontal and vertical resolution separately by determining actual horizontal and vertical separation of the points in each pair (because the calibration target most likely will be skewed slightly relative to the field of view) from the known distance between the points in each pair and taking account of the pixel aspect ratio, then dividing the number of pixels horizontally and vertically between the points in each pair by the actual horizontal and vertical separation of the points in each pair, respectively. Average horizontal and vertical resolution values then would be calculated by averaging the values determined from each of the four point pairs A,C; B,D; E,G; and F,H; or from user-selected point pairs.

Once the system resolution is determined, it is displayed to the user, who raises or lowers the camera to adjust the resolution as necessary. The process is then repeated until the desired resolution is obtained. Preferably, the software has been provided with a desired value for the resolution—either by the user on a case-by-case basis or by the programmer for certain standardized applications—and the computer indicates to the user whether the camera should be raised or lowered to obtain the desired resolution.

Furthermore, it will be appreciated that if a drive motor 36 is provided, particularly with position encoders, the CPU or controller can control raising or lowering of the camera assembly automatically. The controlling software would "know" to raise the camera if the number of pixels per inch is too high, and to lower the camera if the number of pixels per inch is too low. The amount by which the camera is raised or lowered (measured by the encoders) would be a function of the magnitude of the resolution error.

Figure 4:
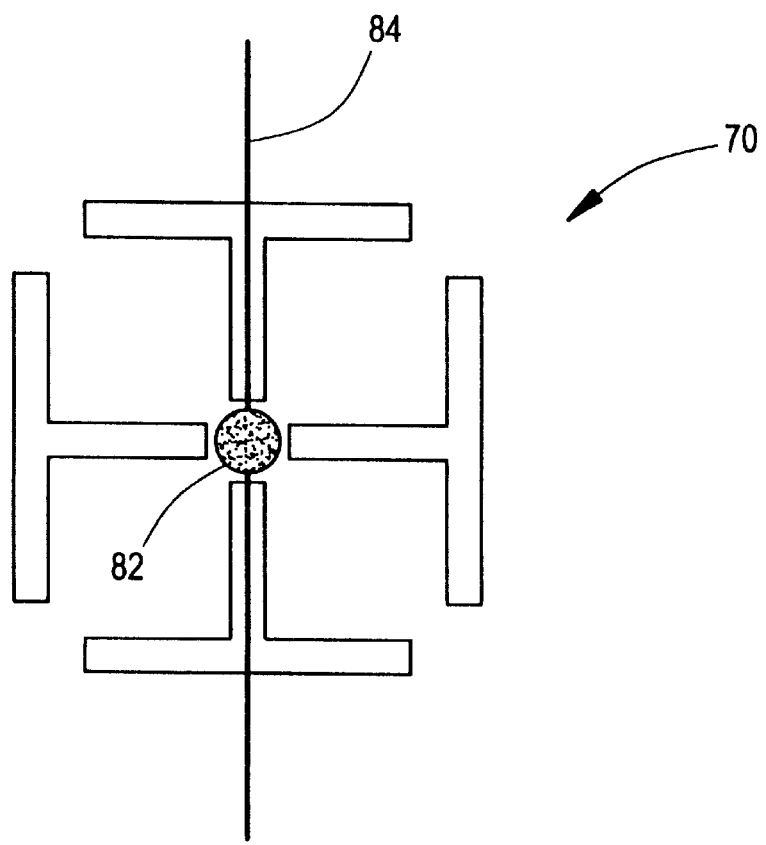
FIG. 4 is a detail view showing the cross of the calibration pattern shown in FIG. 3, with the beams of a spot laser and a line laser converging centrally thereon.

Once the appropriate resolution has been obtained by adjusting (and securing, if desired) the height of the camera assembly, the light sources 38, 40 are illuminated (if not already done so) and are pivoted such that the laser beams 46, 48 fall on and illuminate the calibration target. The conventional, cylindrical beam laser light source is pivoted until the spot 82 of laser light formed thereby lies on the intersection 80, i.e., in the immediate center of the field of view, as shown in FIG. 4. At this point, that light source is locked in position such that its angular orientation with respect to the camera is fixed.

The other light source, i.e., the line laser light source, is then pivoted until the laser line 84 formed thereby is coincident with the dot 82 projected on the target by the first light source, as shown in FIG. 4, and preferably also is coincident with the alignment hashmarks 74. (Using a line laser and a dot laser, as opposed to two dot lasers, facilitates this adjustment.) The second light source is then locked in position so that its angular orientation with respect to the camera is fixed. The two beams 46, 48 thus will converge at the surface of the target 66 with the camera spaced from the target by a distance which results in the desired resolution, as shown in FIG. 2, preferably with the beams intersecting in the center of the field of view.

In embodiments in which laser positioning units 54 and 56 are provided, the image acquisition software can be configured to identify the spot 82 and line 84 formed by the laser light beams and can control the pivoting of the light sources 38, 40 to cause the beams to converge at the target surface.

At this point, the camera system can be used to image other objects having thicknesses or heights above the platform 14 different than the calibration target 66, and to image such objects with the same resolution easily and repeatably. Such an object ("the new object") may be, for example, a gun having a fingerprint which it is desired to photograph and digitize for entry into and/or comparison against a nationwide fingerprint database, or currency being analyzed as counterfeit or legitimate.

The calibration target is removed and the new object is placed under the camera; because the laser beams have been angled to intersect in the center of the field of view, it is easier to position the new object generally centrally within the field of view simply by observing where the laser beams fall on the object. (Unless the new object is the same height as the calibration target, the laser beams no longer will be coincident at the surface of the object, but both beams still most likely will fall on the new object such that they can be used generally to center it.) The camera is then raised or lowered as necessary which, because of the angled nature of the laser beams relative to the optical axis, causes the points at which the laser beams strike the surface of the new object to move as the camera is raised or lowered, and this can be observed quite easily by watching the laser beams move across the object. The camera is adjusted until the laser beams, which have not been re-angled relative to the camera, again converge at the surface of the object whose image is being acquired. It will be appreciated that the point of convergence of the laser beams will lie at the same location within the field of view of the camera as when the laser beams converged at the surface of the calibration target. Thus, at this point the resolution again will have the desired value.

The lasers are then turned off (temporarily) and the image of the object being evaluated is acquired. Preferably, the lasers and the camera are interlocked such that the lasers are automatically shut off while the image is being acquired (whether a still or a video image) so as not to have the acquired image include the laser beams and so as not to saturate the acquired image with the laser light.

If the camera height adjustment is motorized, raising or lowering of the camera to bring the laser beams back into convergence at the surface of the new object—i.e., to bring the resolution back to the desired resolution—can also be controlled by the computer program. The program determines on which side of the laser line the laser dot lies, and from this determines whether the camera is too close to or too far from the new object. The program then causes the camera to be raised or lowered accordingly until the laser dot and laser line converge.

Although for most applications calibrating the camera using the generally flat, planar calibration target 66 provides excellent results, it is known that for any optical image acquisition system, there is a plane of optimal focus which is located generally in the center of the depth of field, with the focus of the system "softening" fore and aft of the plane of optimal focus until the image would be deemed to be out of focus. For certain applications, it is desirable to have the camera lens focus set such that the plane of optimal focus is coincident with the plane at which the resolution is the desired value.

Figure 5:
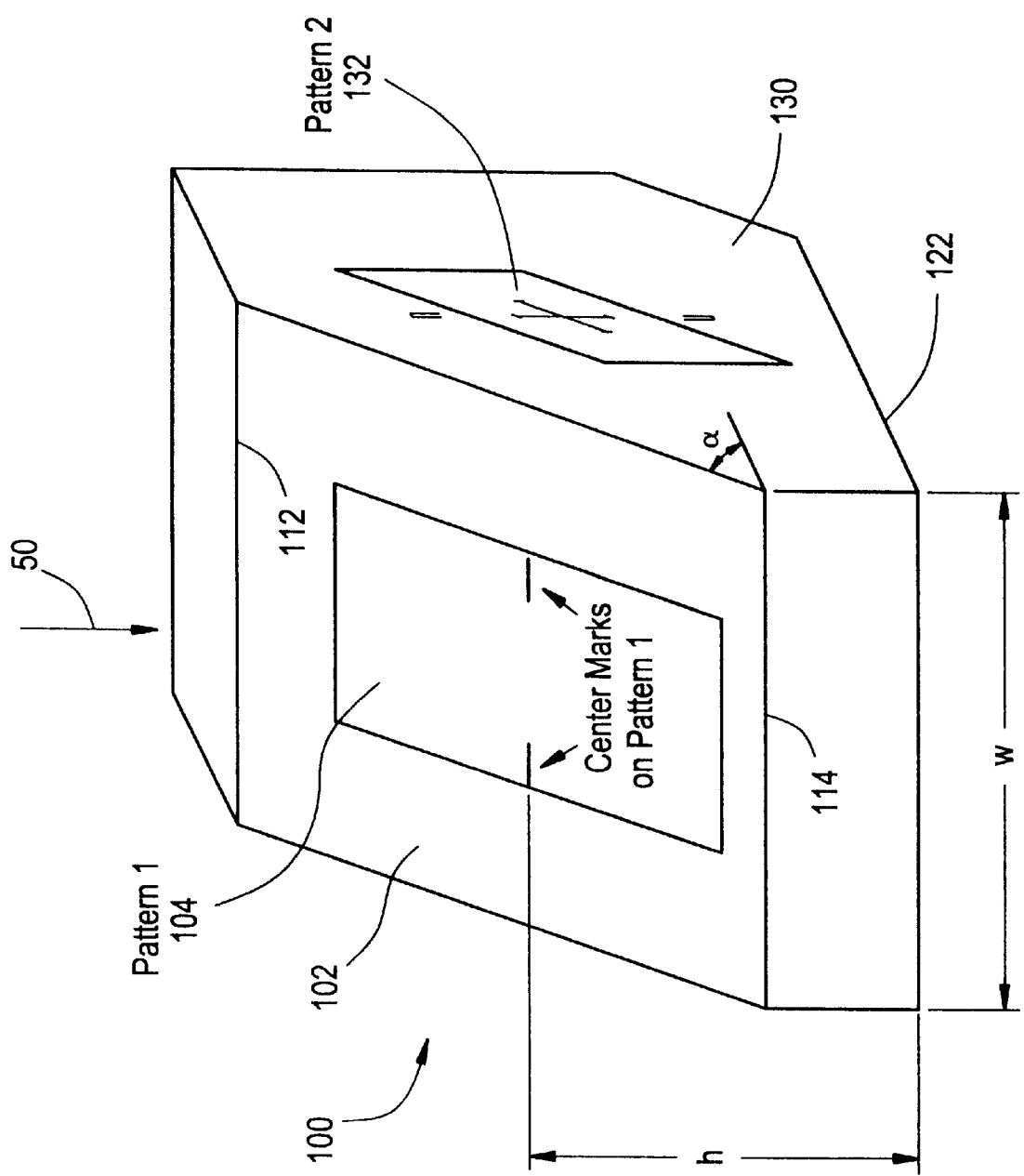
FIG. 5 is a schematic, perspective view showing a calibration block which may be used instead of the calibration target of FIG. 1.
Figure 5A:
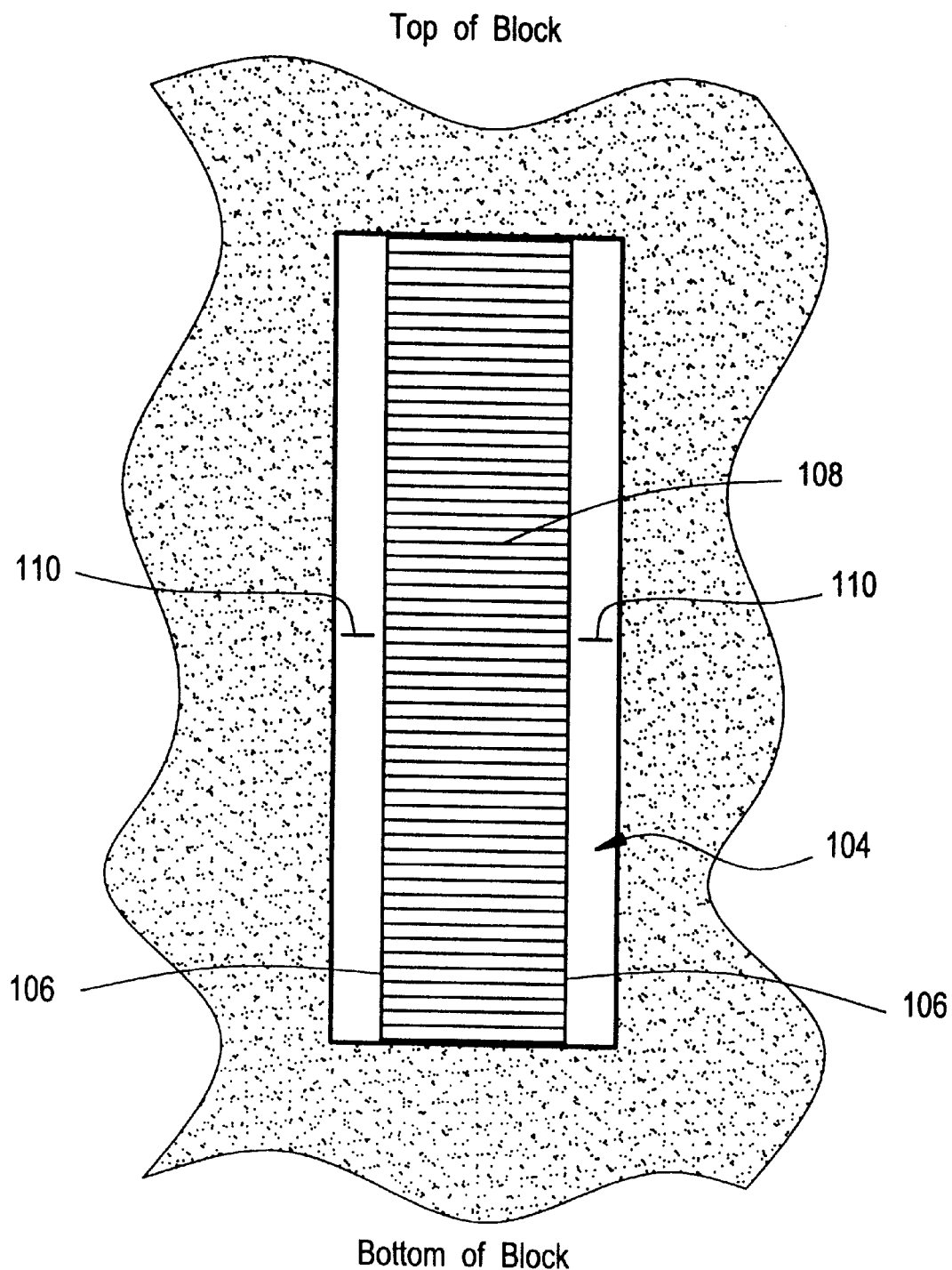
FIG. 5A is a plan view showing the calibration pattern on the inclined surface of the calibration block shown in FIG. 5.

To facilitate this, calibration block 100 has been developed, as shown in FIG. 5. The calibration block has at least one surface 102 which is oriented at a non-perpendicular, non-parallel angle α relative to certain ones of the other surfaces, e.g., 45°. The surface 102 is predominantly black, as indicated by shading, with a central "patch" of white and a first calibration pattern 104 printed in the middle of the patch of white, e.g., a "ladder" pattern as shown in FIG. 5A. The ladder pattern has two precisely spaced, perfectly parallel longitudinal lines 106, and a series of evenly spaced, perfectly parallel cross-lines 108 extending between the lines 106 like the rungs of a ladder. Additionally, the pattern has two center marks 110, perfectly parallel to the cross-lines 108, with one on either side of the pattern. The pattern is positioned on the calibration block with the cross-lines 108 extending parallel to the upper and lower edges 112, 114 of the surface 102 (FIG. 5). Preferably, the size of the pattern is such that it extends beyond the bounds of the field of view of the camera when the pattern is imaged by the camera, at least in terms of the length of the pattern. This maximizes the benefit obtained with the calibration block.

Figure 5B:
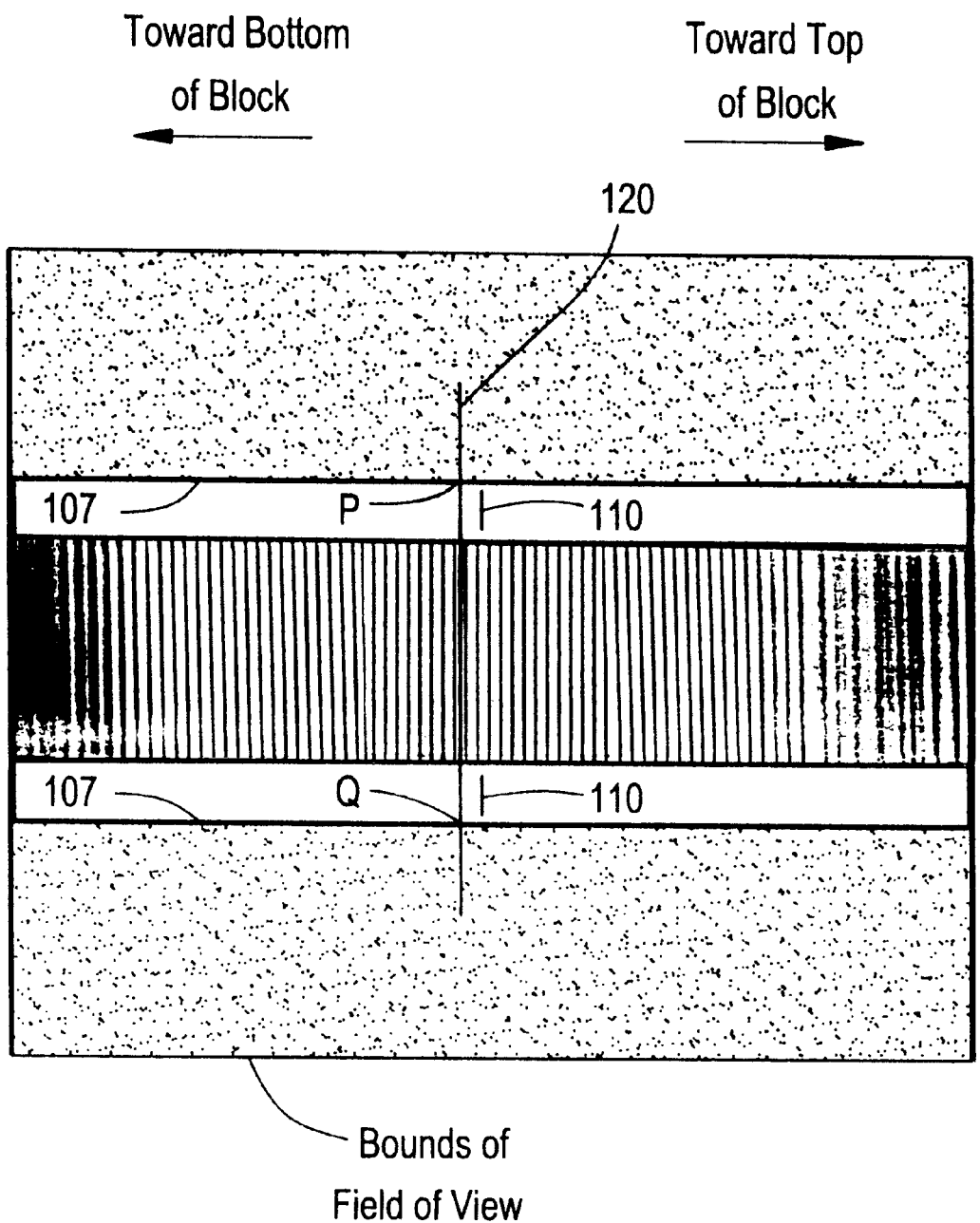
FIG. 5B shows the image of the calibration pattern shown in FIG. 5A, with the central portion thereof in focus and end portions thereof out of focus.

When calibrating the camera, the calibration block 100 is placed on the platform 14 below the camera, represented by the optical axis 50 in FIG. 5. Assuming the field of view is rectangular, it is preferable for the calibration block to be oriented such that the long dimension of the calibration pattern 104 is aligned with the lengthwise direction of the field of view, as indicated in FIG. 5B. Assuming the line laser light source is oriented such that the laser line projected thereby extends vertically within the field of view, the laser line can be used to facilitate this orientation by aligning it with the cross-lines 108 or the two center marks 110. With this orientation, the line laser beam crosses the surface 102 of the calibration block at a uniform distance from the line laser light source, rather than falling across portions of the surface 102 that are at different heights, thereby projecting a sharper, more distinct laser line on the surface of the calibration block.

The angled nature of the surface 102 facilitates setting the plane at which the resolution is the desired value to be coincident with the plane of optimal focus as follows. Because the surface 102 is angled, the end of the pattern 104 that is closer to the top of the block will be closer to the camera, and the opposite end will be further away from the camera. As a result, assuming the camera is adjusted to be focused at a plane that lies between the horizontal plane passing through the top of the pattern and the horizontal plane passing through the bottom of the pattern, the image of the pattern will vary from fuzzy and out of focus at the top of the pattern, to sharp and in focus somewhere in the middle region of the pattern, and back to fuzzy and out of focus at the bottom region of the pattern, as shown in FIG. 5B. (It may be necessary to adjust the size of the camera aperture (f-stop) to achieve this condition.)

Assuming the pattern 104 consists strictly of black lines on a white background, the transition from black to white in the image, going from one cross-line 108 to the next through the intervening space of "opposite" color, will be the sharpest, and therefore the most distinct, at the location of the plane of optimal focus. Accordingly, the software program analyzing the image information can locate the plane of optimal focus by evaluating the differential in light intensity of adjacent pixels and finding the location where this differential is the greatest, corresponding to the sharpest transition from one cross-line to the next. The software package will then display graphically to the user a line 120 (FIG. 5B), cutting across the image, corresponding to the line where the plane of optimal focus intersects the surface 102 of the calibration block 100.

Next, the points P and Q (FIG. 5B) where the line 120 intersects the edges 107 of the black region/white patch are located by the software. The image analysis program calculates the resolution at the plane of optimal focus by determining the number of pixels between those two points and dividing by the distance between the edges 107, which is precisely known and which has been provided to the program.

If the resolution matches the desired resolution, the system is ready to be used to image subsequent objects. If, however, the resolution is not correct, the spacing between the camera and the lens is adjusted using different extension tubes, shims, or a back focus mechanism; the new location of the plane of optimal focus is found; and the resolution at that plane is determined. (Simply raising or lowering the camera, as is done when using the flat calibration target 66, would merely "pull" or "push" the plane of optimal focus up or down with the camera and therefore would not change the resolution at the plane of optimal focus.) This procedure is iterated until the plane of proper resolution coincides with the plane of optimal focus. It will be appreciated that focus and resolution are interrelated; accordingly, it may be necessary to "play" with the system slightly to bring these two planes into coincidence with the correct resolution. If the focus or back focus adjustment is computer-controlled and the height of the camera relative to the calibration block is computer-controlled, the image analysis software can be configured to achieve this goal automatically.

To facilitate cross-checking the calibration, it is preferable to position the pattern 104 on the surface 102 with center marks 110 located a perpendicular distance h (FIG. 5) from the bottom surface 122 of the block that is the same as the width W of the block. The camera is calibrated by adjusting the height of it relative to the block such that the resolution at the horizontal plane passing through the marks 110 is the desired resolution. Once the proper resolution and optimal focus have been achieved at the horizontal plane passing through the centering marks 110, the block is rotated and placed on its side such that surface 130 faces upward and is exposed to the camera. Surface 130 has a second pattern 132 which is identical to the calibration pattern on the calibration target 66, shown in FIG. 3. Because the width w of the calibration block is the same as the height h from the bottom surface 122 to the centering marks 110, the pattern 132 will be positioned at the same distance above the platform 14, when the block is positioned on its side, as the centering marks 110 were. The resolution of the system is then verified by determining the resolution using the second pattern in the manner described above.

Once the resolution is verified, the focus and/or back focus are locked and all parameters are retested to confirm that they have not been changed, and the lasers are angled relative to the camera and locked in position, as described above. This may be done using the second calibration pattern 132, identically to the method described above. Alternatively, the calibration block could be repositioned so that it is oriented as shown in FIG. 5. In that case, the line laser would be angled such that the line projected thereby passes through the center of the field of view (determined by observing the video overlay on the monitor); the calibration block would be positioned such that the laser line passes through the two centering marks 110; and then the conventional laser would be angled such that the laser dot falls on the laser line at the surface 102 and generally in the center of the field of view (also determined by observing the video overlay on the monitor).

The calibration block 100 is then removed from the platform 14 and the camera system is used to image other objects in the same manner described above.

Figure 6A:
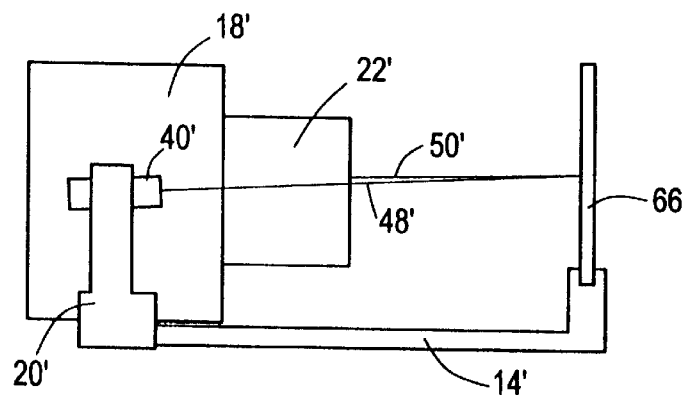
FIGS. 6A and 6B are a schematic, side elevation view and a schematic, plan view, respectively, of a horizontally oriented alternative embodiment of the apparatus shown in FIG. 1.
Figure 6B:
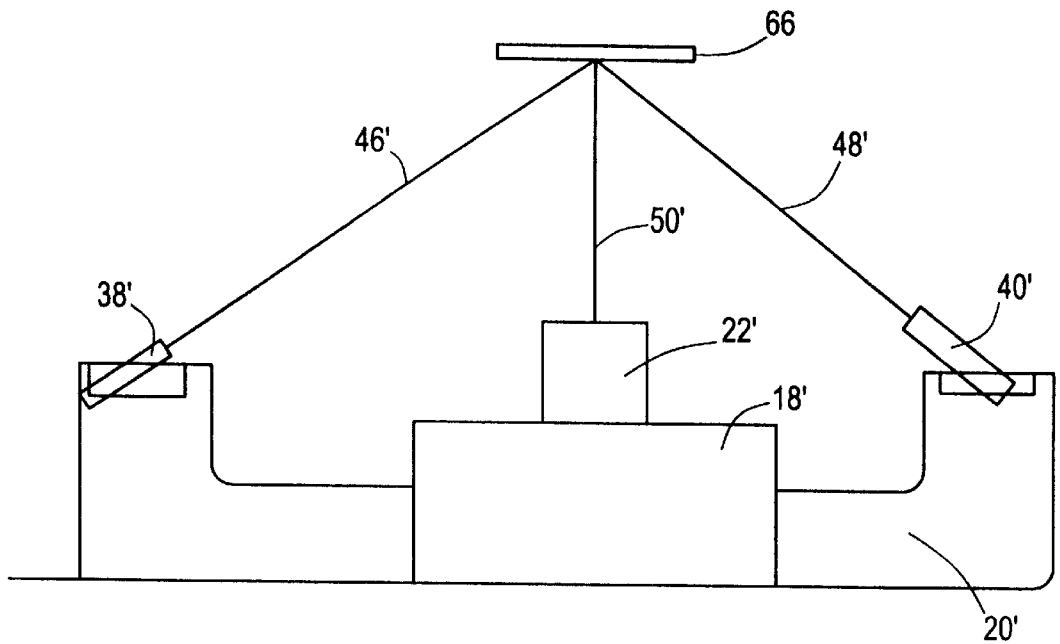
Figure 7:
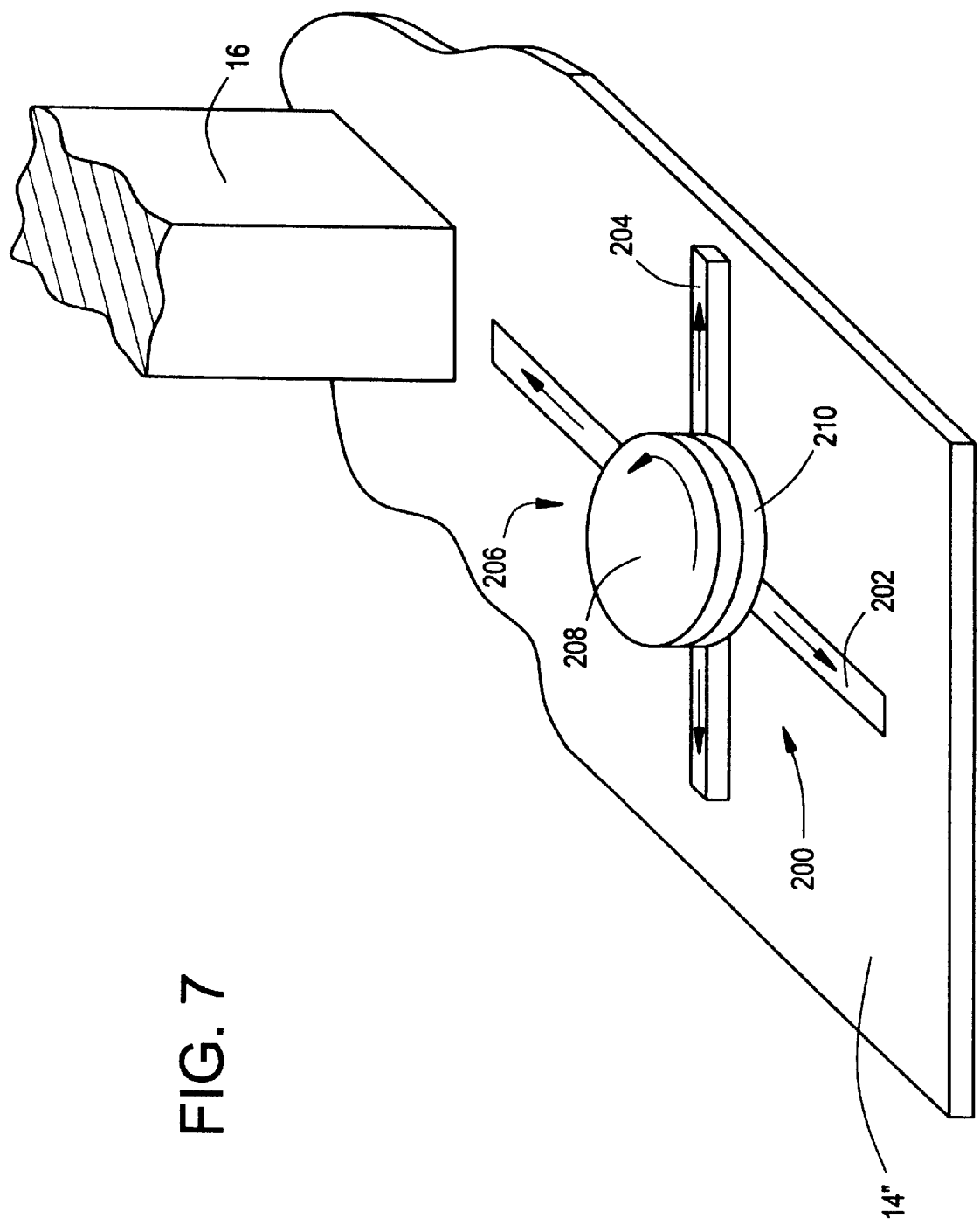
FIG. 7 is a schematic, perspective view, broken away, showing an x-y-θ table incorporated into the embodiment of FIG. 1.

Finally, it will be appreciated that the invention admits of numerous alterations and modifications, all of which are deemed to be within the scope of the invention. For example, although the apparatus and method have been described in connection with a camera located above and aimed down on a target, the system can be constructed so as to be oriented horizontally and/or to be portable for field use, as shown in FIGS. 6A and 6B, wherein elements with primed reference numbers correspond generally to the elements described above with non-primed reference numbers. In this embodiment, bracket 14' is configured to hold the calibration target 66 for alignment of the light sources 38', 40' in the manner described above. The bracket 14' and optics can be pre-configured for a given resolution, or an overlay in the view finder (or on the video monitor) can be used to align the target for a given resolution. Alternatively, the target can be set at any distance (and hence any resolution) and the lights aligned with it. The resolution can then be determined either in the field or later, depending upon available equipment.

The calibration target 66 is then removed and the camera is used to acquire the image of an object of interest, maintaining the camera at the proper distance from the object (and hence resolution) by ensuring that the beams 46', 48' converge at the surface of the object of interest. The camera 18' and laser mounting bracket 20' can be removed from the support bracket 14' and used to acquire the image of an object at any location without being hindered by the support bracket 14', or the assembly can be left intact, with the support bracket 14' being used as a resting device or frame for the object of interest.

If the camera is being held by hand, it may be desirable to add a third or even a fourth laser, adjusting the additional laser(s) such that the beam(s) converge(s) at the surface of the calibration target either with the beams of the first two lasers or, if four lasers are being used, with each other's beam. This facilitates orienting the camera such that the optical axis is normal to the plane of the surface of the object being imaged.

In another alternative embodiment, which provides increased accuracy of the alignment of the calibration target, calibration block, or subsequent object of interest being imaged, the support platform 14" is constructed with an x-y-θ positioning apparatus 200. The positioning apparatus has a first track 202 (which may be recessed in the platform 14" such that its top surface is level with the surface of the platform 14"); a second track 204 which is perfectly perpendicular to the first track 202 and which slides back and forth along the track 202; and an angular orientation table 206, which slides back and forth along the second track 204. The angular orientation table has an upper pallet 208 on which the object being imaged is supported and which itself is supported by and rotates relative to support block 210. The linear and angular position of each of these elements can be controlled with a great degree of precision by means (not shown) which are known and available to those having skill in the art.

Furthermore, although the light sources 38, 40 are shown and described as being positioned such that both of their beams are offset from and angled relative to the optical axis 50, it will be appreciated that the system can be configured such that one of the beams is coincident with the optical axis over at least a portion of the optical axis. This may be achieved by placing a beam splitter in between the camera and the calibration target or other object being imaged, with the beam splitter oriented to allow the camera to acquire the image of the target or object, and shining a laser at the beam splitter from the side such that the beam from that laser is reflected by the beam splitter down along the optical axis 50. The benefit of such an arrangement is that one light source will always illuminate the object at the center of the field of view; the disadvantage (as compared to the configurations described above) is that the accuracy and ease of adjustment provided by having two beams converge or diverge as the camera is moved toward or away from the object being viewed is diminished by fifty percent.

Finally, in a variant of this last-described alternative embodiment, calibration and repeated setting of the resolution of the system can be achieved using only a single offset light source if the location of the center of (or some other fixed location within) the camera's field of view is displayed to the user, e.g., using a video overlay. The user would adjust the camera to obtain the desired resolution, and then the single light source would be pivoted until its beam illuminates the calibration target precisely in the center of (or at the other marked spot within) the field of view. (A spot laser or other dot-producing light source should be used; a line laser would not work as well for this embodiment.) Then, the proper resolution could be required, for imaging any other object, by raising or lowering the camera until the beam illuminates the object at a point that is at the marked, reference position in the field of view.

Further embodiments having other modifications and improvements are deemed to be within the scope of the following claims.

We claim:

1. A high-precision-resolution image acquisition apparatus, said apparatus comprising:

a support surface for supporting an object to be imaged;

a camera supported at an optical distance from said support surface for acquiring an image of an object being imaged, said camera outputting a signal representing the image of said object being imaged and said camera having an optical path along which said image is acquired and a field of view, said image having a resolution and said optical distance being adjustable such that the resolution of said image can be adjusted;

computer means for analyzing said signal to determine the resolution of said image;

a first light source which projects a first beam of light so as to strike said object being imaged at a first location on a surface of said object being imaged, said first light source being configured such that said first location varies as said optical distance is adjusted; and a second light source which projects a second beam of light so as to strike said object being imaged at a second location on said surface of said object being imaged, wherein one of said first and second light sources is a line laser and the other of said first and second light sources is a cylindrical beam laser which projects a dot or spot of laser light on said object being imaged.

2. The apparatus of claim 1, wherein said first light source is configured such that said first beam of light is angled relative to said optical path whereby said first location varies as said optical distance is adjusted.

3. The apparatus of claim 1, wherein said second light source is configured such that said second beam of light is angled relative to said optical path whereby said second location varies as said optical distance is adjusted.

4. The apparatus of claim 1, wherein said first and second light sources are configured such that said first and second beams of light are angled relative to said optical path whereby said first and second locations vary as said optical distance is adjusted.

5. The apparatus of claim 4, wherein said first and second light sources are spaced from said camera and are pivotable relative to said camera whereby said first and second beams of light can be caused to intersect at said surface of said object being imaged such that said first and second locations are coincident.

6. The apparatus of claim 1, wherein said computer means comprise computer hardware.

7. The apparatus of claim 1, wherein said camera is a video camera and said computer hardware comprises a frame grabber.

8. The apparatus of claim 1, wherein said computer means comprise computer software.

9. The apparatus of claim 1, wherein said signal comprises a pixilated representation of said image and wherein said resolution is expressed in terms of pixels per unit of length of said object being imaged.

10. The apparatus of claim 1, further comprising a motor which causes said optical distance to be adjusted.

11. The apparatus of claim 10, wherein said computer means controls operation of said motor to cause said optical distance to be adjusted such that said resolution has a desired value.

12. The apparatus of claim 10, said apparatus further comprising computer means for analyzing said signal to determine said first location, said computer means controlling operation of said motor to cause said optical distance to be adjusted such that said first location is at a desired position.

13. The apparatus of claim 1, further comprising a motor which causes said optical distance to be adjusted.

14. The apparatus of claim 13, said apparatus further comprising computer means for analyzing said signal to determine said first and second locations, said computer means controlling operation of said motor to cause said optical distance to be adjusted such that said first and second locations are coincident.

15. The apparatus of claim 1, further comprising a support platform on said support surface, said support platform permitting precise control of the linear and angular positioning of said object being imaged.

16. The apparatus of claim 1, wherein said first light source and said camera are interlocked such that said first light source does not project said first beam of light as said image is being acquired.

17. A high-precision-resolution image acquisition apparatus, said apparatus comprising:
a support surface for supporting an object to be imaged;
a camera supported at an optical distance from said support surface for acquiring an image of an object being imaged, said camera outputting a signal representing the image of said object being imaged and said camera having an optical path along which said image is acquired and a field of view, said image having a resolution and said optical distance being adjustable such that the resolution of said image can be adjusted;
computer means for analyzing said signal to determine the resolution of said image; and
a first light source which projects a first beam of light so as to strike said object being imaged at a first location on a surface of said object being imaged, said first light source being configured such that said first location varies as said optical distance is adjusted;
wherein said first light source is configured such that said first beam of light is angled relative to said optical path whereby said first location varies as said optical distance is adjusted, said apparatus further comprising a first motor which controls the angle of said first beam of light relative to said optical path.

18. The apparatus of claim 17, said apparatus further comprising computer means for analyzing said signal to determine said first location, said computer means controlling operation of said first motor to cause said first location to be adjusted to a desired position.

19. The apparatus of claim 18, wherein said desired position is the center of the field of view of said camera.

20. A high-precision-resolution image acquisition apparatus, said apparatus comprising:
a support surface for supporting an object to be imaged;
a camera supported at an optical distance from said support surface for acquiring an image of an object being imaged, said camera outputting a signal representing the image of said object being imaged and said camera having an optical path along which said image is acquired and a field of view, said image having a resolution and said optical distance being adjustable such that the resolution of said image can be adjusted;
computer means for analyzing said signal to determine the resolution of said image;
a first light source which projects a first beam of light so as to strike said object being imaged at a first location on a surface of said object being imaged, said first light source being configured such that said first location varies as said optical distance is adjusted;
a second light source which projects a second beam of light so as to strike said object being imaged at a second location on said surface of said object being imaged; and
a first motor which controls the angle of said first beam of light relative to said optical path.

21. The apparatus of claim 20, said apparatus further comprising computer means for analyzing said signal to determine said first and second locations, said computer means controlling operation of said first motor to cause said first location to be adjusted to a desired position, said desired position being coincident with said second location.

22. The apparatus of claim 21, wherein said desired position is at the center of the field of view of said camera.

23. The apparatus of claim 21, wherein said second light source is configured such that said second beam of light is angled relative to said optical path whereby said second location varies as said optical distance is adjusted, said apparatus further comprising a second motor which controls the angle of said second beam of light relative to said optical path, said computer means controlling operation of said first and second motors to cause said first and second locations to be adjusted to be coincident.

24. A method of acquiring the image of an object with a repeatable resolution, said method comprising the steps:

providing a first object;

providing a camera at a first optical distance from said first object, said camera having a field of view and an optical path along which an image is acquired;

positioning said first object within said field of view;

providing a first light source and, with said first light source, projecting a first beam of light so as to strike said first object at a first location on a surface of said first object, said first light source being configured such that said first location varies as said first optical distance is adjusted;

providing a second light source and, with said second light source, projecting a second beam of light so as to strike said first object at a second location on said surface of said first object;

adjusting said first light source to cause said first location to be coincident with said second location whereby said first and second beams of light converge at the surface of said first object;

removing said first object from the field of view;

providing a second object within said field of view at a second optical distance from said camera, said first and second beams of light stirring said second object at third and fourth locations, respectively, on a surface of said second object;

adjusting said second optical distance, if necessary, to cause said third and fourth locations to be coincident without repositioning said first light source, said second light source, or said camera relative to each other, whereby said first and second beams of light converge at the surface of said second object; and acquiring an image of said second object, said method further comprising before adjusting said first light source, 1) acquiring an image of said first object, said image of said first object having a resolution; 2) determining said resolution; and 3) adjusting said first optical distance, if necessary, to cause said resolution to have a desired value.

25. The method of claim 24, wherein said image of said first object is pixilated and wherein said resolution is expressed in terms of pixels per unit of length of said first object.

26. The method of claim 24, wherein said camera is a film-based camera and said resolution comprises a dimension of said first object as shown in said image of said first object divided by a corresponding actual dimension of said first object.

27. The method of claim 24, further comprising removing said second object from the field of view;

providing a third object within said field of view at a third optical distance from said camera;

adjusting said third optical distance, if necessary, to cause said first and second beams of light to converge at the surface of said third object; and acquiring an image of said third object.

28. A method of acquiring the image of an object with a repeatable resolution, said method comprising the steps:

providing a firs t object;

providing a camera at a first optical distance from said first object, said camera having a field of view, an optical path along which an image is acquired, a lens, and a medium on which said image falls;

positioning said fit object within said field of view;

providing a first light source and, with said first light source, projecting a first beam of light so as to strike said first object at a first location on a surface of said first object, said first light source being configured such that said first location varies as said first optical distance is adjusted;

providing a second light source and, with said second light source, projecting a second beam of light so as to strike said first object at a second location on said surface of said first object;

adjusting said first light source to cause said first location to be coincident with said second location whereby said first and second beams of light converge at the surface of said first object;

removing said first object from the field of view;

providing a second object within said field of view at a second optical distance from said camera, said first and second beams of light striking said second object at third and fourth locations, respectively, on a surface of said second object;

adjusting said second optical distance, if necessary, to cause said third and fourth locations to be coincident without repositioning said first light source, said second light source, or said camera relative to each other, whereby said first and second beams of light converge at the surface of said second object; and acquiring an image of said second object;

said method further comprising before adjusting said first light source, 1) acquiring an image of said first object, said image of said first object having a resolution; 2) determining said resolution; and 3) adjusting a distance between said lens and said medium, if necessary, to cause said resolution to have a desired value.

29. The method of claim 28, wherein said image of said first object is pixilated and wherein said resolution is expressed in terms of pixels per unit of length of said first object.

30. The method of claim 28, wherein said camera is a film-based camera and said resolution comprises a dimension of said first object as shown in said image of said first object divided by a corresponding actual dimension of said first object.

31. A method of acquiring the image of an object with a repeatable resolution, said method comprising the steps:

providing a first object;

providing a camera at a first optical distance from said first object, said camera having a field of view and an optical path along which an image is acquired;

positioning said first object within said field of view;

providing a first light source and, with said first light source, projecting a first beam of light so as to strike said first object at a first location on a surface of said first object, said first light source being configured such that said first location varies as said first optical distance is adjusted;

providing a second light source and, with said second light source, projecting a second beam of light so as to strike said first object at a second location on said surface of said first object;

adjusting said first light source to cause said first location to be coincident with said second location whereby said first and second beams of light converge at the surface of said first object;

removing said first object from the field of view;

providing a second object within said field of view at a second optical distance from said camera, said first and second beams of light striking said second object at third and fourth locations, respectively, on a surface of said second object;

determining whether to increase or decrease said second optical distance based on the relative positions of said third and fourth locations on said surface of said second object;

adjusting said second optical distance, if necessary, to cause said third and fourth locations to be coincident without repositioning said first light source, said second light source, or said camera relative to each other, whereby said first and second beams of light converge at the surface of said second object; and acquiring an image of said second object.

32. A method of acquiring the image of an object with a repeatable resolution, said method comprising the steps:

providing a first object;

providing a camera at a first optical distance from said first object, said camera having a field of view a and an optical path along which an image is acquired;

positioning said first object within said field of view;

providing a first light source and, with said first light source, projecting a first beam of light so as to strike said first object at a first location on a surface of said first object, said first light source being configured such that said first location varies as said first optical distance is adjusted;

providing a second light source and, with said second light source, projecting a second beam of light so as to strike said first object at a second location on said surface of said first object;

adjusting said first light and second light sources to cause said first location to be coincident with said second location whereby said first and second beams of light converge at the surface of said first object;

removing said first object from the field of view;

providing a second object within said field of view at a second optical distance from said camera, said first and second beams of light striking said second object at third and fourth locations, respectively, on a surface of said second object;

adjusting said second optical distance, if necessary, to cause said third and fourth locations to be coincident without repositioning said first light source, said second light source, or said camera relative to each other, whereby said first and second beams of light converge at the surface of said second object; and acquiring an image of said second object.

\* \* \* \* \*